United States Patent [19]
Hamilton

[11] Patent Number: 5,989,360
[45] Date of Patent: Nov. 23, 1999

[54] GAS-DRIVEN PORTABLE SELF-CONTAINED VACUUM DEVICE

[76] Inventor: Thomas I. Hamilton, 9100 Serrant Ct., Bakersfield, Calif. 93311

[21] Appl. No.: 08/935,397

[22] Filed: Sep. 23, 1997

[51] Int. Cl.[6] ....................................................... A47L 5/18
[52] U.S. Cl. ................................ 134/21; 15/405; 15/409; 222/635; 239/318
[58] Field of Search ...................... 15/405, 409; 239/318, 239/337; 222/635; 134/21

[56] References Cited

U.S. PATENT DOCUMENTS

| | | | |
|---|---|---|---|
| 2,016,113 | 10/1935 | Lambert et al. | 15/405 X |
| 2,856,205 | 10/1958 | Coleman et al. | 15/409 X |
| 2,968,441 | 1/1961 | Holcomb | 239/337 |
| 3,148,806 | 9/1964 | Meshberg | 239/337 X |
| 3,430,811 | 3/1969 | Nystrom | 15/405 X |
| 3,437,272 | 4/1969 | Abplanalp | 239/318 X |
| 3,578,948 | 5/1971 | Friend et al. | 15/409 X |
| 3,897,004 | 7/1975 | French | 239/318 |
| 3,913,842 | 10/1975 | Singer | 239/337 |
| 4,054,998 | 10/1977 | Hesselgren | 32/33 |
| 4,228,798 | 10/1980 | Deaton | 128/276 |
| 4,350,299 | 9/1982 | Stephenson et al. | 239/337 |
| 4,594,807 | 6/1986 | McQueen | 43/132.1 |
| 4,874,404 | 10/1989 | Boswell | 55/86 |
| 4,961,916 | 10/1990 | Lesage et al. | 422/88 |
| 5,225,158 | 7/1993 | Tayebi et al. | 422/4 |
| 5,317,930 | 6/1994 | Wedding | 73/863.03 |
| 5,364,474 | 11/1994 | Williford, Jr. | 134/32 |
| 5,531,722 | 7/1996 | Van Hale | 604/280 |
| 5,565,677 | 10/1996 | Wexler et al. | 250/251 |

*Primary Examiner*—Chris K. Moore
*Attorney, Agent, or Firm*—Townsend and Townsend and Crew LLP

[57] ABSTRACT

A portable, self-contained vacuum device designed for hand-held use to create a moderate vacuum effect for various applications. A small diameter tube (10) is firmly attached (14) to the nozzle or spray tip of an aerosol canister and inserted at a point (16) through the wall of, and directed in one direction along the interior length of a larger diameter tube (12). The tubes may be fixed to the exterior of the aerosol canister, may be detachable for storage, or may be manufactured into the interior of the aerosol canister. When propellant gas from the aerosol canister is released and injected out of the outflow end (20) of the smaller diameter tube toward one end of the larger diameter tube, the resulting aspiration of ambient gasses creates a vacuum effect at the opposite end, or intake end (18), of said larger diameter tube. A vented receptacle (22) is added to capture the aspirated debris and other matter, but allow the propellant and ambient gasses to pass into the atmosphere through filter screens (28) of desired permeability. The use of antiseptic additives with the aerosol propellant provides enhancement for use of the device for biological waste collection purposes. The use of preservative additives with the aerosol propellant provides enhancement for use of the device for specimen collection purposes.

12 Claims, 6 Drawing Sheets

GAS-DRIVEN PORTABLE SELF-CONTAINED VACUUM DEVICE

BACKGROUND

1. Field of Invention

This invention relates to portable, self-contained vacuum devices used primarily for cleaning purposes, for medical/dental uses, for specimen collection, or to evacuate air from storage containers for perishable goods.

2. Description of Prior Art

Devices in which a vacuum is created by an air pump driven by an electric motor have been used for decades to gather material, whether for household cleaning, for clearing fluid accumulations during medical or dental procedures, for specimen collection, for evacuating air from food storage containers, and for use in the creative arts. These devices generally have concentrated on applications not requiring portability or self-containment, and have therefore relied upon electric power to drive them. In recent decades, personal size vacuums for cleaning purposes have been developed, but they still generally rely upon electricity, either alternating current or direct current battery (often-rechargeable) power. None of these devices achieve the true portability and self-containment of the claimed invention. Recently, vacuum cleaning devices have yielded to a less effective means of cleaning, especially for consumer electronic devices, in the form of aerosol canisters which discharge dry blasts of gasses to blow away dust and debris. The preference for the aerosol canister cleaning devices is primarily attributable to their hand-held portability rather than any superior cleaning function.

Dust and other small particles have become a serious problem for consumer electronics as well as scientific apparatus of all types. With the large scale introduction of computers and other electronic devices into homes and other locations where climatic and other environmental circumstances are not carefully controlled, dust and particulate trash are constantly being deposited on critical mechanical and electronic components of these complex and expensive devices. The accumulation of unwanted dust and trash can cause short circuits to electronic components and can jam mechanical functions causing permanent damage or other serious problems. The need has arisen for compact, self-contained, readily accessible means for periodically cleaning the particles and other debris from these devices to prevent the damaging and potentially dangerous effects of its accumulation.

Simple wiping or brushing can damage delicate parts, and can cause static electricity discharges, which can permanently damage electronic components. The aerosol containers of compressed gasses recently mass marketed with success in the consumer market, are touted as an effective means of cleaning electronic devices using short, highly-directed blasts of gas intended to blow debris off of delicate components. Various combinations of gasses, with various forms of nozzles and blast-directing devices, have been widely accepted in the consumer market due to their convenience, portability, low cost, and long shelf life. However, the use of blasts of compressed gas as a cleaning method is flawed in concept not only because it fails to remove the unwanted debris from the work environment, but also because it can cause dust and debris to roll or "snowball" into more damaging accumulations and can even force the unwanted debris deeper into components where it might become less retrievable and cause greater damage. If a device were available which was just as portable and convenient, with similar shelf-life and of roughly the same cost, but which physically lifted or removed the unwanted debris from the work environment, then such device should meet with wide acceptance and commercial success.

Certain vacuum devices for small areas have been marketed primarily for use in medical and dental applications, but those proposed have depended on electrical pumps to create the vacuum and have been far from portable. Patents related to these inventions have focused on trapping medical/dental wastes in a manner that prevents them from contaminating the area and infecting others. A method and apparatus for disinfecting fluid medium removed from the oral cavity of a human being has been patented, U.S. Pat. No. 4,054,998, to Hesselgren (1975), which claims to disinfect human saliva and blood, and rinsing fluids, by passing them through a disinfecting zone in which the potentially infectious media is mixed with a disinfectant. However, the media is transported through the device by means of a vacuum created by an electric motor, and is not portable. Separately, a suction receptacle with hygroscopic filter has been patented, U.S. Pat. No. 4,228,798, to Deaton (1979), whereby a hygroscopic filter is used to absorb and retain fluid particles and prevent the passage of potentially infectious waste. This device depends on a vacuum drive created by an electric motor, and therefore also is not portable. The present invention allows for total portability and self-containment, lending itself to application for the decentralized provision of medical and dental health care in remote locations.

The present invention uses a vacuum generated by aspiration created upon the release of gas from an aerosol canister. An aspiration unit has been patented, U.S. Pat. No. 5,531,722, to Van Hale (1994) which, instead of depending on the release of gas to create a vacuum effect from aspiration, depends upon an external vacuum source (presumably powered by electricity) to create the flow which causes the aspiration which is the main point of the Van Hale patent.

A crawling pest eliminator system and method, U.S. Pat. No. 4,594,807, to McQueen (1985) has been patented to eliminate crawling pests, which is a function closely similar to, and subsumed in, specimen collection. The McQueen device is purported to be portable, in that it includes in its design a shoulder harness to permit carrying on one's back. However, this level of portability does not compare to the hand-held portability and electricity-free operation of the present invention. The McQueen device might have greater endurance because of its electrical power supply, but its dependence on an electric motor does not provide as much utility for application in remote field locations as does the present invention.

Generally, vacuum creating devices for small area cleaning or for medical or dental uses or for specimen collection have suffered from one or more of a number of disadvantages:

a) They are not portable.

b) They are not convenient to use in tight working conditions, such as work benches or craft areas.

c) They require electricity for operation.

d) They do not capture specimens and small debris in a sanitary manner.

e) They are not easy to maneuver by hand.

f) Battery driven devices are heavy and do not have a long shelf life.

g) Their replacement parts are complicated and expensive.

h) They are not amenable to mass distribution in consumer markets.

Objects and Advantages

Accordingly, besides having the advantages lacking in the devices currently considered the state of the art, as described above, several objects and advantages of the present invention are:

a) The invention, though not obvious, is readily adapted from devices currently marketed with great success.

b) The invention does not merely disperse unwanted debris but rather gathers it in a manner that would permit its total removal from the workspace.

c) The invention is convenient to use and can be operated simply with one hand by simply placing the nozzle of the device at the location from which the debris or specimen is to be removed, then releasing the aerosol propellant.

d) It has a long shelf life, lasting as long as the device remains charged with aerosol propellant.

e) There are no batteries or motor or pump parts to wear out.

f) It is totally self-contained.

g) It can be manufactured in a fashion that makes it economical enough to be disposable.

h) By using various additives in the propellant, the invention can easily apply an evenly dispersed application of disinfectant, preservative, or the like to the collected debris or specimens, thereby treating the captured debris or specimen at the same moment that it is collected.

i) It is amenable to applications for household cleaning, electronic repairs, medicine, dentistry, food preservation, and crafts.

Further objects and advantages of the invention will become apparent from a consideration of the drawings and ensuing description.

DRAWING FIGURES

In the drawings, closely related figures have the same number but different alphabetic suffixes.

SUMMARY

Reference Numerals in Drawings

Figure 1A:
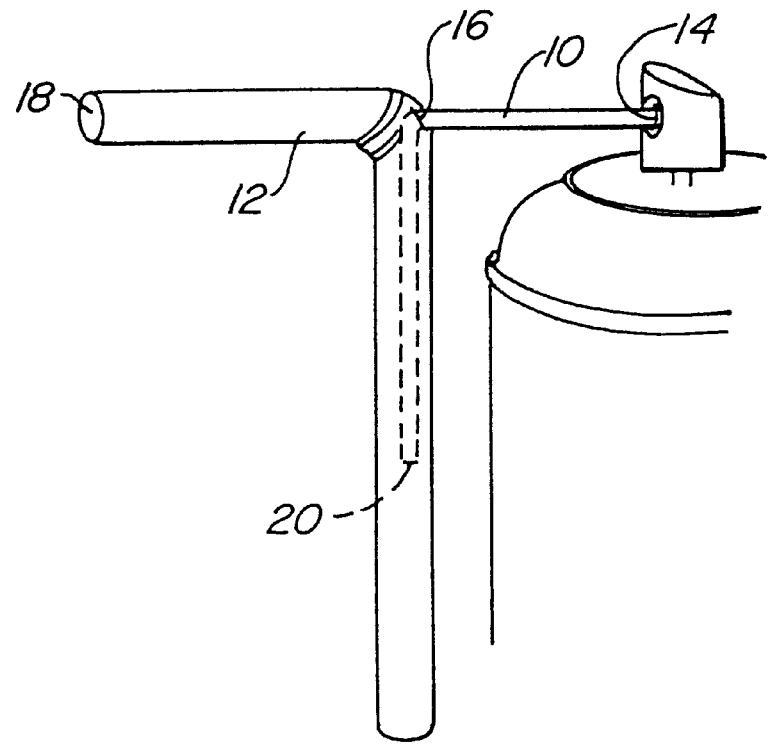
FIGS. 1A and 1B show an overall view, and a more detailed partial view, of the device, attached to the spray nozzle of a conventional aerosol canister.

| 10 | small diameter tube | 12 | larger diameter tube |
|---|---|---|---|
| 14 | attachment to aerosol nozzle | 16 | insertion point into large tube |
| 18 | intake of large tube | 20 | aerosol outflow of small tube |

-continued

Reference Numerals in Drawings

| 22 | vented receptacle | 24 | aerosol canister cap |
|---|---|---|---|
| 26 | canister cap as vented receptacle | 28 | screen filters over vents |
| 30 | insertion point into receptacle | 32 | large tube coiled for storage |
| 34 | pointed nozzle | 36 | elbow nozzle |
| 38 | narrow elongated nozzle | 40 | slant tip elongated nozzle |
| 42 | Iarge tube within canister | 44 | small tube within canister |
| 46 | modified aerosol nozzle | 48 | bands attaching to canister |

In accordance with the present invention, a portable, self-contained vacuum device comprises a small diameter tube attached to the nozzle or spray tip of a canister containing propellant gas and inserted through the wall of, and directed in one direction along the interior length of, a larger diameter tube, thereby causing propellant gas released from the canister containing propellant gas and injected out of the smaller diameter tube toward one end of the larger diameter tube, to cause the aspiration of ambient gasses into, and create a vacuum effect at, the opposite end of said larger diameter tube.

DESCRIPTION OF THE INVENTION

FIGS. 1–6

Figure 1B:
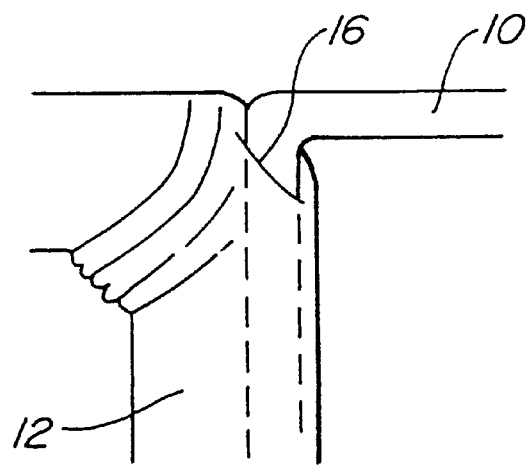

A simple embodiment of the vacuum device of the present invention is illustrated in FIG. 1A. The device has a small tube 10 one end of which is attached to the aperture of the spray nozzle of an aerosol canister. The attachment 14 of said small tube to said aerosol canister is accomplished by wedging said end of said small tube 10 into the small aperture of the standard spray nozzle which is designed for the purpose of receiving similar tubes. Said end of said small tube 10 is made of such material, and is of such size, that the attachment 14 to the spray nozzle of the aerosol canister is tight enough to remain fixed during use. Otherwise, said small tube 10 can be of any material which does not bend of its own weight. The opposite end of said small tube 10 is the outflow end 20 of said small tube and is directed into and through an insertion point 16 through the wall of, and along the interior length toward one end of, a larger diameter tube 12. Here, the small tube 10 is shown to be rigid, with a single ninety degree (90°) bend. In FIG. 1A, the bend in the small tube is inside the larger tube 12. In FIG. 1B, the bend in the small tube 10 is outside the larger tube 12.

Depending upon the embodiment, the small diameter tube 10 might, or might not, be permanently affixed with a tight seal at the insertion point 16 into the larger tube 12. If the action of the aerosol spray nozzle requires, the small tube 10 might fit more loosely to slide in and out of the insertion point 16 opening into the larger tube 12.

The larger diameter tube 12 can be of any material, which generally does not collapse from atmospheric pressure when the desired vacuum effect is created. In FIG. 4B, a separate embodiment indicates that it is important that the material for the larger tube 12 to be flexible enough that it may be wound into a coil 32 for storage purposes. For all other embodiments, said larger tube 12 will more frequently be of rigid plastic or metal or other durable material which permits it to be permanently affixed to the aerosol canister. In any event, said larger tube 12 must be rigid enough for its intake end 18 to be maneuvered and directed to the location from which material is to be removed by the vacuum effect of the device.

Figure 2:
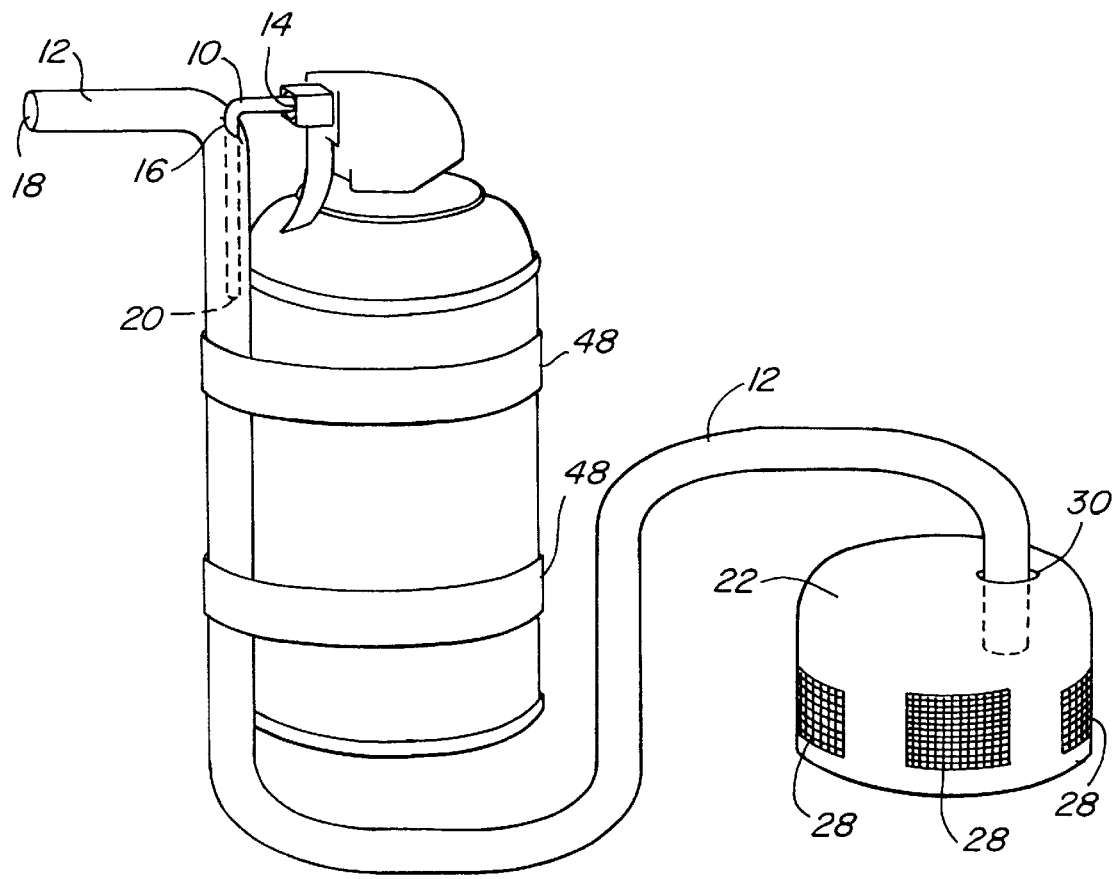
FIG. 2 shows the device with a simple vented receptacle to collect aspirated material.

A more elaborate embodiment is depicted in FIG. 2, showing the larger tube 12 elongated to reach a detached vented receptacle 22, which acts as a containment vessel for matter collected by the larger tube's intake 18. The opposite end of said larger tube 12 is inserted into the insertion point into the receptacle 30, in order to deposit the aspirated debris and other matter into the vented receptacle 22. The vents of the vented receptacle 22 typically are lined with filter medium, or with fine mesh, to act as a filter screen 28, which retains within the vented receptacle 22 whatever debris or other material is being collected. The permeability of the filter paper, or the size of the mesh of any screen, used as a filter screen 28 in the vents of said vented receptacle 22 is dictated by the size of debris or other material which is intended to be captured.

Figure 3:
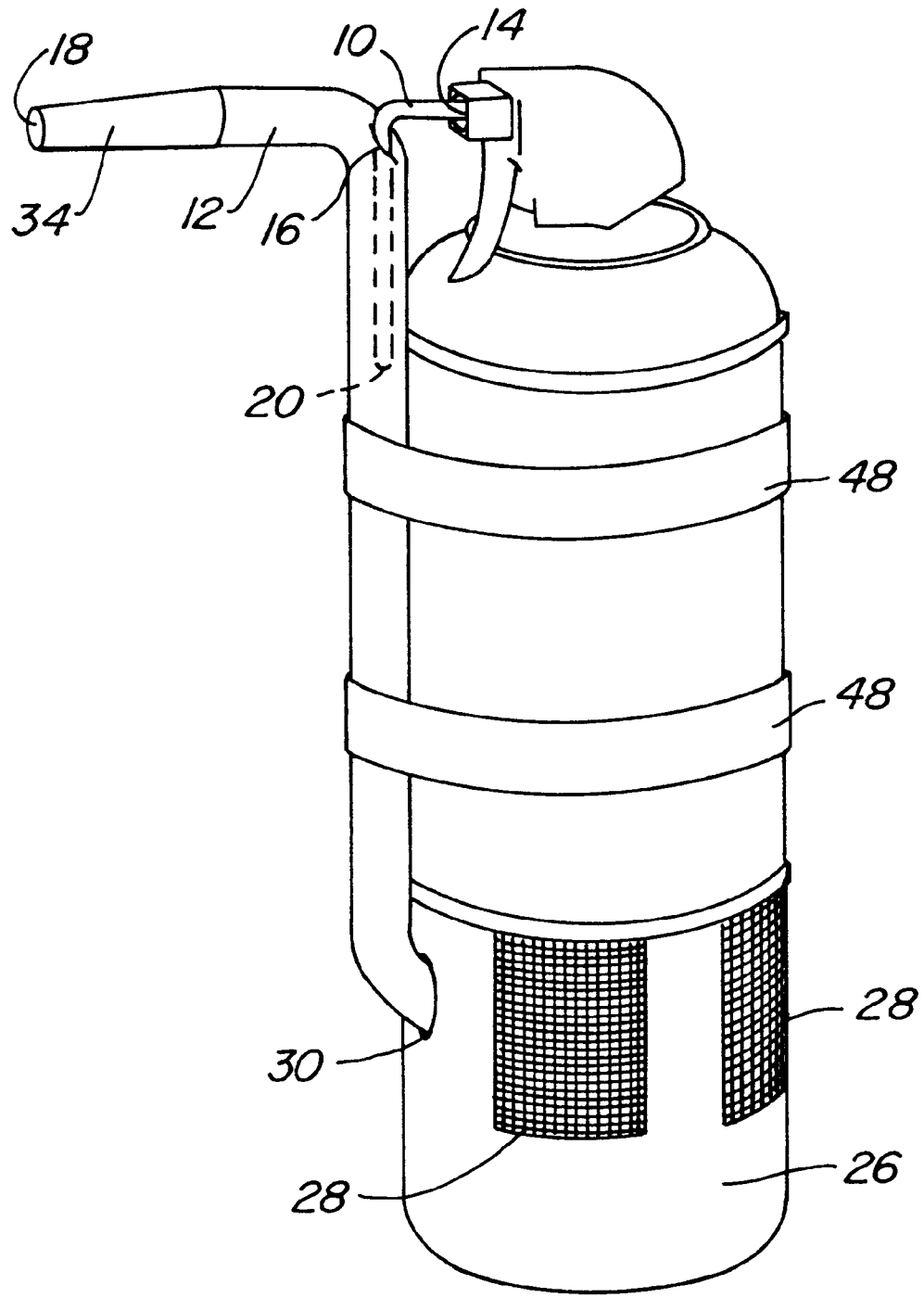
FIG. 3 shows the device with a vented receptacle fit to the bottom of the aerosol which it is attached.

Yet another embodiment of the invention is depicted in FIG. 3, which shows the basic device first indicated above, with the further addition of the vented receptacle being affixed to the bottom of the aerosol canister, for portability and ease of use. FIG. 3 also shows the addition of a pointed nozzle attachment 34, which has a tapered tip with an intake opening which has a diameter no larger than the inner diameter of the thinnest portion of the remainder of said larger tube 12 minus the outer diameter of the small tube 10, in order to minimize clogging within the larger tube 12 where the presence of the small tube 10 otherwise limits the throughput capacity of said larger tube 12. FIG. 3 demonstrates one of many means for attaching the larger tube 12 to the aerosol canister, here accomplished with two wide bands 48 of appropriate material such as rubber, plastic, or metal.

Figure 4A:
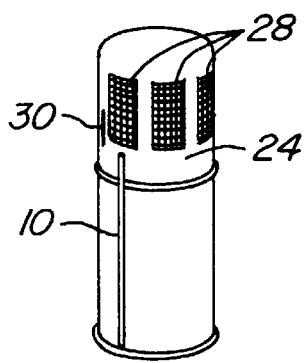
FIGS. 4A through 4C show the device with the cap of the aerosol canister to which the device is attached as a storage device for parts of the device (as configured for the storage shelf), in a disassembled view to show the contents as stored, and assembled for use with the cap as a receptacle fit to the bottom of the aerosol canister to gather aspirated material.
Figure 4B:
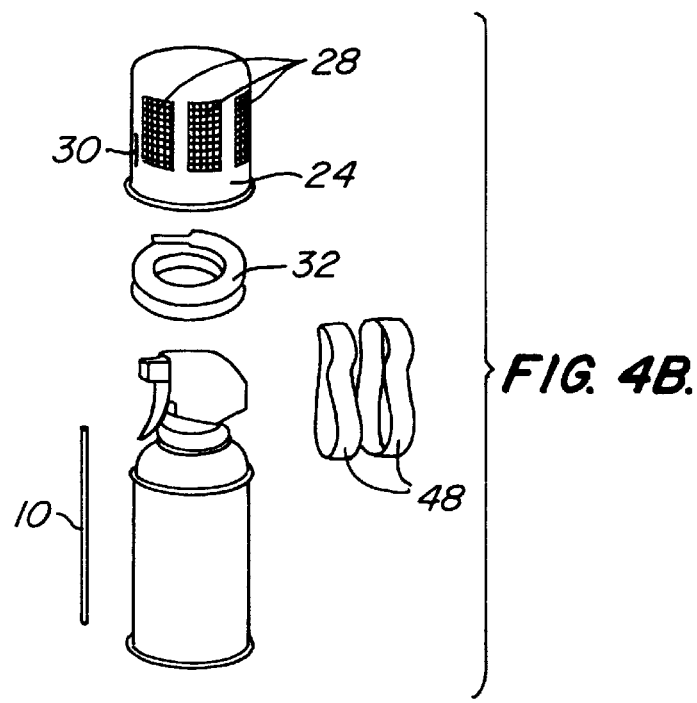

FIGS. 4A through 4B depict a novel embodiment of the vacuum device of the invention, in that they show how an aerosol might be configured for marketing to the consumer. In FIG. 4A, the small tube 10 is simply affixed by cellophane tape or other means to the outside of the aerosol canister, with the vented receptacle 26 attached as the cap 24 of the aerosol canister. FIG. 4B shows how the components for the device might be stored inside the aerosol canister cap 24, and then reassembled in the configuration shown in FIG. 4C for operation, and then configured more permanently in FIG. 4D with bands 48 attaching the larger tube 12 to the aerosol canister.

Figure 5A:
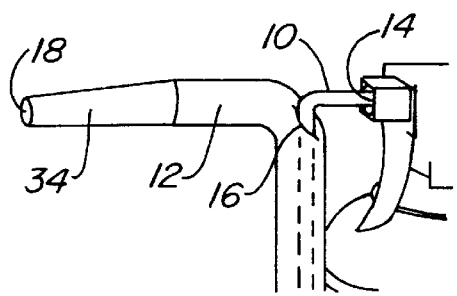
FIGS. 5A through 5D show sample nozzle attachments for the intake end of the larger diameter tube where the vacuum effect is created.
Figure 5B:
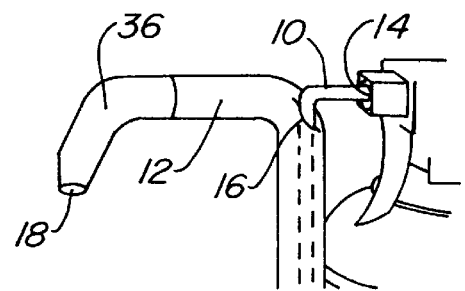
Figure 5C:
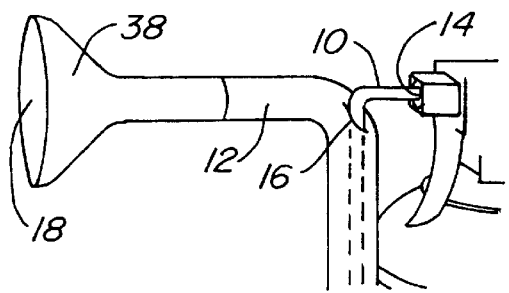
Figure 5D:
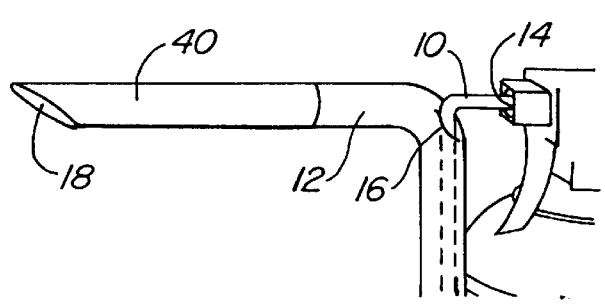

FIGS. 5A through 5C simply depict examples of various nozzle attachments for the intake of the larger tube 18, which might be fashioned for special uses. The pointed nozzle 34 of FIG. 5A is described above. The elbow nozzle 36 of FIG. 5B, which can be manufactured in various lengths and sizes, can be oriented in any direction and is designed to reach around corners where it would otherwise be difficult for the intake of the larger tube 18 to reach. FIG. 5C shows a narrow width, elongated aperture nozzle 38, which would fit in between rows of delicate components. A final example of the many shapes and sizes of nozzles which might be fashioned is shown in FIG. 5D, as a flat elongated nozzle with slant tip 40 which would fit into narrow crevices.

Figure 6:
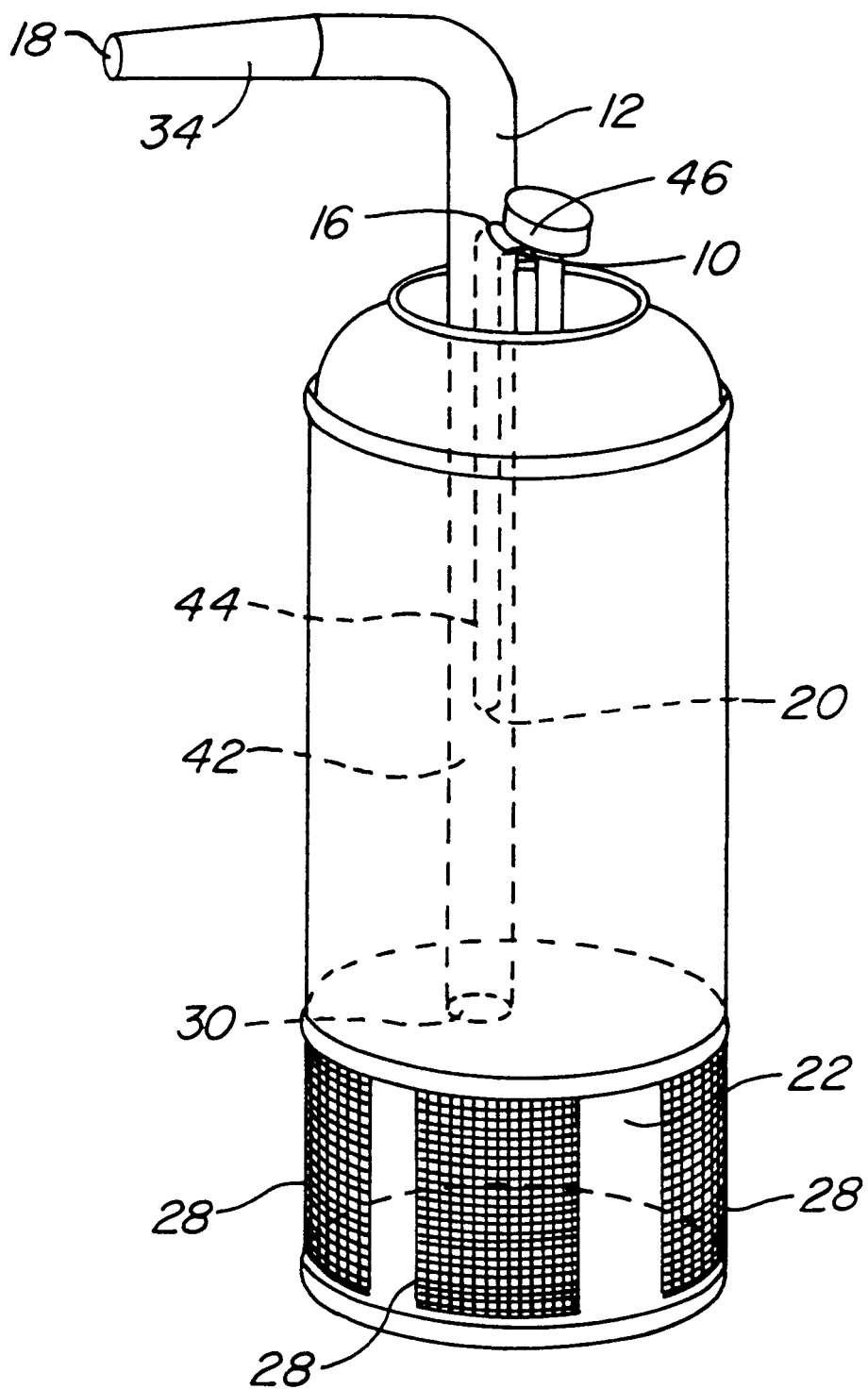
FIG. 6 shows the device contained primarily within the interior of an aerosol canister.

FIG. 6 shows an embodiment of the vacuum device of the invention, which requires special manufacture of the aerosol canister. This embodiment provides that the larger tube is placed within the aerosol canister 42, and that the small tube also runs inside the canister 44, down the interior length of said larger tube within the canister 42. The larger tube within the canister 42 passes down the interior of the canister, and empties the aspirated debris and other material into the vented receptacle 22 affixed to the aerosol canister, which is lined with filter screens 28 over its vents, where said debris and material is collected for disposal or evaluation. This embodiment requires a modified aerosol nozzle 46, which, when depressed with a finger, releases the aerosol propellant back down through the small tube 10 to aspirate material into the intake of the larger tube 18 (here through the pointed nozzle 34) and direct it out through the insertion point into the receptacle 30.

OPERATION OF THE INVENTION

FIGS. 1, 2, 3, 4, and 6

The manner of using the vacuum device, which comprises the present invention, is very similar to the manner of using those devices currently on the market for cleaning electronic components using blasts of compressed aerosol gas.

In its most general configuration, shown in FIGS. 1A and 1B, the user holds the aerosol canister in one hand, and points the intake of the large tube 18 toward, and almost touches, the material or debris which is desired to be aspirated. Next, the user depresses, or otherwise activates, the spray nozzle of the aerosol canister, releasing the aerosol propellant gas through the small tube which then forces it out of the small tube outflow 20 in a directional path toward one end of the larger diameter tube 12. The aerosol propellant gas thus propelled through the larger diameter tube 12 aspirates ambient gasses and matter at the intake of the larger tube 18, thereby creating a vacuum effect and transporting said gasses and matter through and out the entire length of said larger tube 12.

The embodiment shown in FIG. 2 operates in precisely the same manner as that shown in FIGS. 1A and 1B, only it further depicts a vented receptacle 22, into which the larger tube 12 empties all aspirated material. Aerosol propellant gas, and ambient gasses aspirated into the intake of the large tube, pass into the vented receptacle 22 and out of the vents lined with filter screens 28 (comprised of filter paper or appropriate mesh screen, depending on the material being collected) leaving the debris and or other non-gaseous aspirated material in the receptacle for disposal or evaluation.

The embodiment shown in FIG. 3 operates identically to the embodiment shown in FIG. 2, except that the vented receptacle is affixed to the bottom of the aerosol canister. In this particular figure, the vented receptacle is the aerosol canister cap 26, fitted to the bottom of the canister.

Figure 4C:
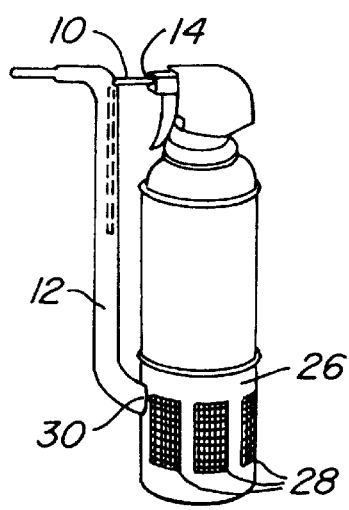
Figure 4D:
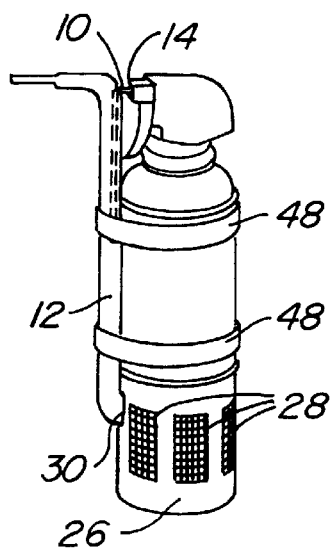

FIGS. 4A through 4D show an embodiment which permits ready marketing of the device, configured as shown in FIG. 4A. FIG. 4B shows the aerosol canister with its cap removed, and with its contents displayed. FIG. 4C shows the basic assembly of the device, using the parts, which were, contained in the aerosol canister cap when packaged, and FIG. 4D shows the assembled device, ready for operation.

FIG. 6 shows an embodiment that would require special manufacture of the aerosol canister itself, but would eliminate the need for external parts to be assembled onto the outside of the aerosol canister. The operation is identical to the other embodiments described above, except primarily for two items. First, the unit includes the large tube within the aerosol canister 42. Second, this embodiment also has the small tube within the aerosol canister 44. The only external appendages would be the larger tube 12 itself, and the modified aerosol nozzle 42. The modified aerosol nozzle directs the aerosol propellant through the small tube within the canister 44, and forces gas through the large tube within the canister 46, creating aspiration and the desired vacuum effect at the selected nozzle 34 attached to the intake of the large tube 18, and depositing the aspirated debris and other matter in the vented receptacle 22. Meanwhile, the aerosol propellant gas and ambient gasses escape through the screen filters of the vents 28 of said vented receptacle 22.

Each of the foregoing embodiments can be adapted for special applications by mixing specific additives with the aerosol propellant, such that the aspirated matter which is collected in the vented receptacle 22 is evenly exposed to, and comes in contact with, such additives. By way of example, a disinfectant can be added to the aerosol propellant when the embodiment is applied to applications where biological matter or infectious waste is collected. Moreover, specialized preservatives can be added to the aerosol propellant when the embodiment is intended to be used for the collection of specimens for study.

SUMMARY, RAMIFICATIONS, AND SCOPE

Accordingly, the reader will see that this invention, attached to an aerosol canister, creates a simple, easy-to-use, completely portable and self-contained vacuum creating device which has manifold applications for use in small areas where maneuverability is important. The embodiment of the invention can occur with varying lengths and diameters of tubing. Moreover, the function of the invention is relatively independent of the materials used in its manufacture, except for those applications in which flexible material is required. Moreover, for many of the applications, airtight interfaces are not required, however in medical/dental and specimen collection applications where biological hazards are possible, tight fittings and seals at the juncture of all components is important for biological containment.

The invention allows efficient cleaning of delicate work areas, such as components of sophisticated electronic equipment, by permitting the removal of waste material and debris from the work environment rather than simply blowing it into and around the ambient environment where it might cause damage. Obviously, the configuration and shape of nozzles can be as specialized as the particular applications for which the invention is used. Figured nozzle tips are examples only.

The invention, with proper antiseptic additives in the aerosol propellant and with filtered waste receptacles, allows for the collection of biological waste matter during the performance of medical/dental procedures, even in remote locations where electricity is not reliable and sometimes is not even available.

The invention allows for the collection of biological, mineral, botanical, and other specimens, without human contamination. With proper preservative additives in the aerosol propellant, the invention provides an easy method for preserving the specimens in the field to the maximum extent possible.

The invention allows a convenient means for sanitary evacuation of air from food storage containers, such as polypropylene bags, which are closed with twist tie closures, thereby extending the storage life of prepared and leftover foods.

Although the description above contains many specificities, these should not be construed as limiting he scope of the invention but as merely providing illustrations of some of the presently preferred embodiments of this invention. For example, the device could provide a means for recovering lost articles where access is difficult, for initiating a siphon effect in tubes to drain aquariums or small fountains, for holding delicate parts during delicate assembly procedures, for pet grooming, for activating action toys, et cetera. Thus the scope of the invention should be determined by the appended claims and their legal equivalents, rather than by the examples given.

I claim:

1. A vacuum device comprising:

a canister including pressurized propellant gas;

a normally closed outlet on the canister for permitting the propellant gas to discharge upon opening of the normally closed outlet;

a first smaller tube attached to the normally closed outlet of the canister for receiving propellant gas discharged from the normally closed outlet on the canister;

a second, larger tube having an inlet, an outlet, and an entrance for the first smaller tube between the inlet and the outlet of the second, larger tube; and, the first smaller tube received into the second, larger tube at the entrance for the first smaller tube and extending from the entrance toward the outlet of the second larger tube whereby when the normally closed outlet on the canister is open, propellant gas discharges to the outlet of the second, larger tube to create a vacuum at the inlet of the second, larger tube.

2. The vacuum device of claim 1 further comprising:

the inlet of the second, larger tube has an inner diameter no greater than-an interior diameter of the narrowest part of the second, larger tube less the diameter of the first smaller tube.

3. The vacuum device of claim 1 further comprising:

the entrance for the second, larger tube is an aperture through the wall of the second, larger tube.

4. The vacuum device of claim 1 further comprising:

a receptacle connected to the outlet of the second, larger tube to receive the gas discharged from the outlet of the second, larger tube.

5. The vacuum device of claim 4 further comprising:

the receptacle is a vented receptacle.

6. The vacuum device of claim 1 further comprising:

the inlet of the second, larger tube has a shape different than the rest of the second, larger tube.

7. The vacuum device of claim 1 further comprising:

the canister contains a propellant gas.

8. In the combination of:

a canister including pressurized propellant gas;

a normally closed outlet on the canister for permitting the propellant gas to discharge upon opening of the normally closed outlet; and, a first smaller tube attached to the normally closed outlet of the canister for receiving propellant gas discharged from the normally closed outlet on the canister, the improvement to the combination comprising:

a second, larger tube having an inlet, an outlet, and an entrance for the first smaller tube between the inlet and the outlet of the second, larger tube; and, the first smaller tube for being received into the second, larger tube at the entrance for the first smaller tube and for extending from the entrance toward the outlet of the second, larger tube whereby when the normally closed outlet on the canister is open, propellant gas discharges to the outlet of the second, larger tube to create a vacuum at the inlet of the second, larger tube.

9. The improvement to the combination of claim 8 and further comprising:

apparatus for holding the first smaller tube and the second, larger tube to the side of the canister.

10. A process for cleaning small debris from a working site comprising the steps of:

providing a canister including pressurized propellant gas including a normally closed outlet on the canister for permitting the propellant gas to discharge upon opening of the normally closed outlet;

providing a first smaller tube attached to the normally closed outlet of the canister for receiving propellant gas discharged from the normally closed outlet on the canister;

providing a second, larger tube having an inlet, an outlet, and an entrance for the first smaller tube between the inlet and the outlet of the second, larger tube; and, inserting the first smaller tube into the second, larger tube at the entrance for the first smaller tube and extending the first smaller tube from the entrance toward the outlet of the second larger tube, opening the normally closed outlet on the canister to cause propellant gas discharge to the outlet of the second, larger tube to create a vacuum at the inlet of the second, larger tube to cause small debris to travel from the inlet to the outlet of the second, larger tube.

11. A process for cleaning small debris from a working site according to claim 10 and wherein:

the small debris is medical debris.

12. A process for cleaning small debris from a working site according to claim 10 and wherein:

the small debris is specimens to be gathered.

* * * * *